United States Patent [19]

Ohmura et al.

[11] Patent Number: 4,565,651
[45] Date of Patent: Jan. 21, 1986

[54] METHOD OF LYOPHILIZING COLD INSOLUBLE GLOBULIN

[75] Inventors: Takao Ohmura, Takarazuka; Yutaka Hirao; Takuji Hanamura, both of Toyonaka; Akimasa Ohmizu, Hirakata; Satoshi Funakoshi, Katano, all of Japan

[73] Assignee: The Green Cross Corporation, Osaka, Japan

[21] Appl. No.: 538,572

[22] Filed: Oct. 3, 1983

[30] Foreign Application Priority Data

Oct. 7, 1982 [JP] Japan ................................. 57-176917

[51] Int. Cl.$^4$ ...................... C07G 7/00; A61K 35/14
[52] U.S. Cl. ............................. 260/112 B; 260/121; 424/101; 514/8; 514/21
[58] Field of Search ........................... 260/121, 112 B; 424/101, 177; 514/8, 21

[56] References Cited

U.S. PATENT DOCUMENTS

| 3,637,640 | 1/1972 | Huber | 424/177 X |
|---|---|---|---|
| 3,933,996 | 1/1976 | Charlton et al. | 424/177 X |
| 4,085,095 | 4/1978 | Bick et al. | 260/112 B |
| 4,278,594 | 7/1981 | Amrani | 260/112 B |
| 4,305,871 | 12/1981 | Shanbrom | 260/112 B |
| 4,315,906 | 2/1982 | Gelder | 260/112 B X |
| 4,327,086 | 4/1982 | Fukushima et al. | 424/101 X |
| 4,341,764 | 7/1982 | Wallace et al. | 424/101 |
| 4,424,206 | 1/1984 | Ohmura et al. | 424/101 |
| 4,440,679 | 4/1984 | Fernandes et al. | 260/112 B X |

OTHER PUBLICATIONS

Kirk et al., Encyclopedia of Chemical Technology, vol. 3, 1964, 2d Edition, pp. 572–573.

Primary Examiner—Howard E. Schain
Attorney, Agent, or Firm—Cushman, Darby & Cushman

[57] ABSTRACT

A lyophylized cold insoluble globulin preparation can be prepared in stable condition and in short time by lyophylizing an aqueous solution of a cold insoluble globulin in the presence of albumin and a neutral amino acid, a monosaccharide, a disaccharide or a sugar alcohol. The preparation dissolves in water without occurrence of turbidity and is usable for injection.

10 Claims, No Drawings

METHOD OF LYOPHILIZING COLD INSOLUBLE GLOBULIN

BACKGROUND OF THE INVENTION

This invention relates to a method of lyophilizing a cold insoluble globulin.

The cold insoluble globulin (hereinafter referred to as CIG) as hitherto been called "large external trypsin sensitive protein (LETS)", "cell surface protein (CSP)", "cell adhesion factor (CAF)", "opsonic $\alpha_2$ surface binding glycoprotein (O-$\alpha_2$ SBG)" or other, but recently it is generally called CIG or fibronectin. It is a glycoprotein having a molecular weight of 440,000 which occurs in, besides plasma, mesenchymal cells such as fibroblasts or basilar membranes such as epidermis. With regard to other known physicochemical properties of CIG, there may be mentioned that the mobility is that of $\alpha_2$ globulin, the isoelectric point is 5.0, the molecular extinction coefficient $A_{1\,cm}^{1\%}$ 280 nm is 12.9–13.0, S 20, W is 11–14 S, and the carbohydrate content is 5%.

When blood coagulates, the bonding between $\gamma$-chains of fibrin is accelerated by the transglutaminase action of the blood coagulation factor XIII and cross-links of fibrin are formed. In this instance, cross-links between $\alpha$-chains of fibrin are formed through CIG by the catalytic action of the same factor XIII, and thereby the blood coagulation becomes more complete. CIG has also the function of effecting the adhesion or bonding between cells and between cell sustentacular tissues and hence has a pharmacological effect of promoting the wound healing of a trauma. Pharmacological effects hitherto reported of CIG include the treatment of septic shock and the treatment of infective disease on the basis of its enhancing the opsonic action of phagocytes. Moreover, it is known that CIG has an anticancer or antileukemia effect due to its actions of enhancing the intercellular adhesion and of necrotizing cancer cells. Accordingly vast expectations are put on the clinical effect of CIG as a medicine.

When utilized as a medicine, CIG is desired to be made up into lyophilized preparations because of its poor storage stability in solution. When lyophilized, CIG is kept stable to lyophilization by adding thereto a neutral amino acid, monosaccharide, disaccharide, or sugar alcohol as a stabilizer. However, the use of the above stabilizer is undesirable for providing CIG as a medicine, since the dissolution of the lyophilized preparation in distilled water for injection use requires relatively long time and leaves fibrous insoluble matter or develops turbidity.

In view of the above, the present inventors made extensive studies and have found that, when albumin together with at least one stabilizer selected from neutral amino acids, monosaccharides, disaccharides, and sugar alcohols is added to a CIG-containing aqueous solution before lyophilization, the time for dissolving the lyophilized preparations in distilled water for injection use is reduced, the insoluble matter or in consequence the turbidity does not develop, and additionally the stability of CIG to lyophilization is improved synergistically. Based on this finding, this invention has been accomplished.

Thus, this invention relates to a method of lyophilizing a CIG aqueous solution in the presence of albumin and at least one stabilizer selected from the group consisting of neutral amino acids, monosaccharides, disaccharides, and sugar alcohols, the amounts of albumin and the stabilizer being sufficient for preventing the occurence of turbidity of the aqueous solution of the lyophilized CIG.

It is known that CIG is generally obtained by the isolation from fractionated plasma protein, fibroblasts, or culture fluids of fibroblasts.

The method of this invention is applied to CIG purified in a pharmaceutically acceptable degree and desirable contents of protein (including CIG) therein are 0.1–10% W/V. The purified CIG used in this invention may be prepared by any method and is preferably one which has been subjected to heat-treatment for inactivating hepatitis virus. For instance, CIG obtained by the process of heating at 45° C.–52° C. for purifying CIG (Japanese Patent Application Laid-Open No. 121220/83) and the heat treatment at 60° C. for 10 hours for the purpose of inactivating heptatis virus (European Patent Application Laid-Open No. 0058993) is preferably lyophilized by the method of this invention.

According to the heat treatment disclosed in the European Patent Application Laid-Open No. 0058993, CIG which may have hepatitis virus activity can be virus-inactivated with keeping at a minimum the damage of the cold insoluble globulin by heating its aqueous solution at 50° to 80° C. for 5 to 20 hours in the presence of 10% (W/V) or more of at least one principal stabilizer of neutral amino acids, monosaccharides, disaccharides, and sugar alcohols.

The stabilizer to be added to CIG is the same as in the European Patent Application and includes, for example, glycine, alanine, valine, leucine, and isoleucine as neutral amino acids, i.e. monoaminomonocarboxylic acids; glucose, mannose, galactose, and fructors as monosaccharides; sucrose, maltose, and lactose as disaccharides; and mannitol, sorbitol, and xylitol as sugar alcohols; but they are not limited to the above examples. The amount of the stabilizer to be added is however smaller and is approximately 1–10% W/V in combination with albamin added, for preventing the occurrence of turbidity when the lyophilized CIG is dissolved in water.

The albumin to be added to CIG is preferably prepared by purification from pooled plasma of normal human adults in a known way such as a fractionation with methanol, followed by treatment at 60° C. for 10 hours to inactivate hepatitis virus. The amount of albumin to be added is in the order of 0.01–5% W/V, preferably 0.25–0.5% W/V for the above purpose.

The symbol of "% W/V" means the concentration of a solute (g) in 100 ml of the solution, throughout the disclosure and claims.

The lyophilized preparation is usable for injection to a patient after being dissolved in distilled water.

This invention is illustrated in more detail with reference to the following Examples; however it is not restricted by these Examples.

EXAMPLE

Hepatitis virus inactivated CIG obtained by the processes of Japanese Patent Application Laid-Open No. 121220/83 and European Patent Application Laid-Open No. 0058993 were dialyzed against a phosphate-sodium chloride buffer solution. To the resulting solution were added 5% W/V of sucrose and 0.25% W/V of albumin and the CIG concentration was adjusted to 20 mg/ml. This solution was filtered to remove microorganisms, and 2-ml portions of the filtrate were placed separately in 10-ml tubes and lyophilized under such a drying condition that the temperature finally reached 30° C.

The moisture content in the lyophilized preparation was measured in accordance with the general testing method of "The Biological Preparation Standard" (issued by Saikin Seizai Kyokai—literally "Microorganism Preparation Association", July 16, 1979). The found moisture content was 0.2% by weight.

The lyophilized preparation, on adding 2 ml of distilled water for injection use, dissolved immediately, giving a colorless clear solution.

The CIG survial rate in this solution was determined by the single radial immunodiffusion method and the opsonic activity measuring method using fine hepatic pieces [Molnar, J., et al., Biochemistry, 18, 3909 (1979)]. The found values by both the methods were not different at all from those before lyophilization.

EXPERIMENTAL EXAMPLE

Experiments were conducted in order to confirm the stabilizing effect of this invention. In the experiments, specimens of the CIG solution prepared according to the methods of the above Experiment, after albumin and various stabilizers had been added singly or in combination of albumin with the stabilizer (the amounts added are shown Tables 1 and 2), were lyophilized and measured for the various items shown in the Tables.

The results indicated that; when only one of the various stabilizers and albumin was added, the dissolution of the lyophilized preparations required considerable times and the resulting solutions were cloudy or contained fibrous insoluble matter (Table 1); but when albumin was added in combination with one of the various stabilizers, the lyophilized preparations dissolved within one or several minutes and the resulting solutions were colorless and clear (Table 2).

TABLE 1

| Stabilizer | Concentration of stabilizer (W/V %) | CIG survival rate (%) | Opsonic activity survival rate (%) | Moisture content (%) | Finished state after lyophilization | Time for dissolving (min) | Appearance of solution |
|---|---|---|---|---|---|---|---|
| Mannitol | 2 | 88 | 81 | 1.0 | Good | 30 | Slightly cloudy |
| Glycine | 2.25 | 75 | 63 | 2.3 | Good | >30 | Cloudy |
| Sucrose | 5 | 100 | 92 | 0.2 | Good | 15 | Fibrous insoluble matter was observed |
| Glucose | 5 | 100 | 92 | 0.3 | Good | 115 | Fibrous insoluble matter was observed |
| Albumin | 1 | 100 | 90 | 1.2 | Good | 12 | Fibrous insoluble matter was observed |
| None | | 64 | 42 | 2.3 | Shrinked | Sparingly soluble | Cloudy |

TABLE 2

| Concentration of stabilizer (W/V %) | Concentration of albumin (W/V %) | CIG survival rate (%) | Opsonic activity survival rate (%) | Moisture content (%) | Finished state after lyophilization | Time for dissolving (min) | Appearance of solution |
|---|---|---|---|---|---|---|---|
| Sucrose (5) | 0.01 | 100 | 96 | 1.6 | Slightly shrinked | 10 | Fibrous insoluble matter was observed |
| | 0.05 | 100 | 100 | 0.9 | Good | 2–3 | Fibrous insoluble matter was observed |
| | 0.1 | 100 | 100 | 0.4 | Good | <1 | Colorless and clear |
| | 0.25 | 100 | 100 | 0.7 | Good | <1 | Colorless and clear |
| | 0.5 | 100 | 100 | 0.7 | Good | <1 | Colorless and clear |
| | 1.0 | 100 | 100 | 0.5 | Good | <1 | Colorless and clear |
| Glucose (5) | 0.01 | 100 | 93 | 1.9 | Slightly shrinked | 10 | Fibrous insoluble matter was observed |
| | 0.05 | 100 | 100 | 0.6 | Good | 2–3 | Fibrous insoluble matter was observed |
| | 0.1 | 100 | 100 | 0.5 | good | 2–3 | Fibrous insoluble matter was observed |

TABLE 2-continued

| Concentration of stabilizer (W/V %) | Concentration of albumin (W/V %) | CIG survival rate (%) | Opsonic activity survival rate (%) | Moisture content (%) | Finished state after lyophilization | Time for dissolving (min) | Appearance of solution |
|---|---|---|---|---|---|---|---|
| | 0.25 | 100 | 100 | 0.2 | good | <4 | Colorless and clear |
| | 0.5 | 100 | 100 | 0.8 | Good | <1 | Colorless and clear |
| | 1.0 | 100 | 100 | 0.6 | Good | <1 | Colorless and clear |
| Glycine (2.25) | 0.01 | 72 | 55 | 1.8 | Slightly shrinked | 30 | Cloudy |
| | 0.05 | 81 | 62 | 0.8 | Slightly shrinked | 20 | Cloudy |
| | 0.1 | 95 | 82 | 1.8 | Good | 2-3 | Slightly cloudy |
| | 0.25 | 100 | 85 | 1.3 | Good | 2-3 | Fibrous insoluble matter was observed |
| | 0.5 | 100 | 90 | 0.6 | Good | 2-3 | Colorless and clear |
| | 1.0 | 100 | 90 | 0.9 | Good | 2-3 | Colorless and clear |
| Mannitol (2) | 0.01 | 94 | 86 | 0.7 | Slightly shrinked | 20 | Slightly cloudy |
| | 0.05 | 100 | 95 | 1.8 | good | 10 | Fibrous insoluble matter was observed |
| | 0.1 | 100 | 95 | 1.5 | Good | 2-3 | Fibrous insoluble matter was observed |
| | 0.25 | 100 | 100 | 0.8 | Good | 2-3 | Colorless and clear |
| | 0.5 | 100 | 100 | 0.5 | Good | <1 | Colorless and clear |
| | 1.0 | 100 | 100 | 0.5 | Good | <1 | Colorless and clear |

What is claimed is:

1. A method of lyophilizing an aqueous solution of a cold insoluble globulin containing from about 0.1 to 10% w/v cold insoluble globulin which has been purified by heat treatment to a pharmaceutically acceptable degree, said method comprising lyophilizing the aqueous solution to which from about 0.25 to 5% w/v albumin and from about 1 to 10% w/v of at least one stabilizer selected from the group consisting of neutral amino acids, monosaccharides, disaccharides, and sugar alcohols have been added, the amounts of albumin and the stabilizer being sufficient for preventing the occurrence of turbidity when the lyophilized cold insoluble globulin is dissolved in water.

2. The method according to claim 1, wherein the aqueous solution contains the cold insoluble globulin in a concentration of 0.1 to 10% W/V.

3. A lyophylized cold insoluble globulin composition which contains a cold insoluble globulin, albumin and at least one member selected from the group consisting of neutral amino acids, monosaccharides, disaccharides and sugar alcohols.

4. A lyophylized cold insoluble globulin composition prepared by the method of claim 1.

5. The method according to claim 1, wherein the stabilizer is a neutral amino acid and is glycine, alanine, valine, leucine or isoleucine.

6. The method according to claim 1, wherein the stabilizer is a monosaccharide and is glucose, mannose, galactose or fructose.

7. The method according to claim 1, wherein the stabilizer is a disaccharide and is sucrose, maltose or lactose.

8. The method according to claim 1, wherein the stabilizer is a sugar alcohol and is mannitol, sorbitol or xylitol.

9. The method according to claim 1, wherein the amount of albumin is in the range of about 0.5 to about 1.0% w/v.

10. In a method of lyophilizing an aqueous solution of a cold insoluble globulin comprising lyophilizing the solution in the presence of at least one stabilizer selected from the group consisting of neutral amino acids, monosaccharides, disaccharides, and sugar alcohols, the improvement comprising including in the solution to be lyophilized from about 0.25 to 5% w/v of albumin and from about 1 to 10% w/v of said stabilizer, provided that the amounts of albumin and stabilizer are sufficient for preventing the occurrence of turbidity when the lyophilized cold insoluble globulin is dissolved in water.

* * * * *